United States Patent [19]

Abe et al.

[11] Patent Number: 5,097,073
[45] Date of Patent: Mar. 17, 1992

[54] PRODUCTION OF ALIPHATIC PRIMARY OF SECONDARY AMINE

[75] Inventors: Hiroshi Abe; Tohru Katoh; Hisakazu Tajima, all of Wakayama; Kohshiro Sotoya, Naga, all of Japan

[73] Assignee: Kao Corporation, Tokyo, Japan

[21] Appl. No.: 713,835

[22] Filed: Jun. 12, 1991

Related U.S. Application Data

[63] Continuation of Ser. No. 447,515, Dec. 7, 1989, abandoned.

[30] Foreign Application Priority Data

| Dec. 7, 1988 | [JP] | Japan | 63-309409 |
| Dec. 7, 1988 | [JP] | Japan | 63-309410 |
| Sep. 7, 1989 | [JP] | Japan | 1-232568 |

[51] Int. Cl.$^5$ .......................................... C07C 209/48
[52] U.S. Cl. .................................. 564/493; 564/490; 502/331
[58] Field of Search ................. 564/490, 493; 502/331

[56] References Cited

U.S. PATENT DOCUMENTS

| 2,165,515 | 5/1937 | Schmidt | 564/493 |
| 2,225,059 | 12/1940 | Lazier | 564/490 |
| 2,811,556 | 10/1957 | Shapiro | 564/490 |
| 3,260,752 | 7/1966 | Miller et al. | 564/490 |
| 3,444,205 | 5/1969 | Frohlich et al. | 564/490 |
| 3,673,251 | 6/1972 | Frampton et al. | 564/490 |
| 3,845,062 | 10/1974 | Henecka et al. | 564/490 |
| 3,987,099 | 10/1976 | Hockele et al. | 564/491 |
| 4,003,933 | 1/1977 | Drake | 564/493 |
| 4,210,604 | 7/1980 | Müller et al. | 564/480 |
| 4,278,567 | 7/1981 | Miya et al. | 502/331 |
| 4,598,058 | 7/1986 | Frank et al. | 564/490 |
| 4,683,088 | 7/1987 | Oudejans et al. | 564/490 |

FOREIGN PATENT DOCUMENTS

| 0259911A1 | 3/1987 | European Pat. Off. |
| 0232097A3 | 8/1987 | European Pat. Off. |
| 0384542A1 | 8/1990 | European Pat. Off. |
| 2755687A1 | 8/1978 | Fed. Rep. of Germany |
| 1504323 | 10/1967 | France |
| 773432 | 4/1957 | United Kingdom |

OTHER PUBLICATIONS

Chem. Abstracts, vol. 101, Col. 72260m. (1984).
Chem. Abstracts, vol. 84, Col. 179646z. (1976).
Chem. Abstracts, vol. 81, Col. 119919a (1974).

*Primary Examiner*—Richard L. Raymond
*Assistant Examiner*—Scott C. Rand
*Attorney, Agent, or Firm*—Wenderoth, Lind & Ponack

[57] ABSTRACT

Disclosed is a process for preparing an unsaturated aliphatic primary or secondary amine from the corresponding unsaturated aliphatic nitrile without hydrogenating an olefinic bond in the molecule. The process employs a catalyst which is a combination of copper and a specific metal.

6 Claims, No Drawings

PRODUCTION OF ALIPHATIC PRIMARY OF SECONDARY AMINE

This application is a continuation of application Ser. No. 07/447,515 filed on Dec. 7, 1989, now abandoned.

FIELD OF THE INVENTION

The present invention relates to a process for preparing an aliphatic primary or secondary amine from an aliphatic nitrile.

BACKGROUND OF THE INVENTION

An aliphatic primary or secondary amine, especially one containing an unsaturated group, is very useful for many applications or as intermediate. The amine is generally prepared by hydrogenating an unsaturated aliphatic nitrile in the presence of a catalyst for hydrogenation.

For producing the aliphatic secondary amine, copper-chromium catalyst is proposed in UK Patent 773,432. However, since the copper-chromium catalyst is poor in catalyst activity, it takes a long time to terminate the reaction. Japanese Kokai Publication (unexamined) 55-9018 proposes a nickel containing catalyst which, however, hydrogenates a unsaturated group in the molecule as well as a nitrile group. Accordingly, it is difficult to selectively produce the unsaturated secondary amine. In order to resolve the above problems, Japanese Kokai Publication (unexamined) 62-175445 discloses that the hydrogenation is carried out in the presence of a nickel containing catalyst and a carboxylic amide. In this reaction, the carboxylic amide is brought into the reaction product and is quite difficult to remove or separate from the product.

For producing the aliphatic primary amine, Japanese Patent Publication (examined) 38-21353 teaches that the hydrogenation of the unsaturated aliphatic nitrile is carried out in the presence of Raney nickel or Raney cobalt as well as an alkali (alkali metal hydroxide) or ammonia. This method also hydrogenates not only a nitrile group but also an unsaturated group. It therefore is difficult to selectively produce the unsaturated primary amine.

SUMMARY OF THE INVENTION

It has been found that, when copper is combined with a specific metal and employed as catalyst for hydrogenation, an unsaturated aliphatic secondary or primary amine is selectively prepared from an unsaturated aliphatic nitrile, wherein the olefinic group remains unsaturated in the molecules. The process is applicable to the production of the aliphatic secondary or primary amine having an unsaturated group, and is also effective for producing the saturated aliphatic secondary or primary amine from the corresponding saturated nitriles.

Accordingly, the first object of the present invention provides a process for preparing an aliphatic secondary amine comprising reacting a $C_8$–$C_{24}$ aliphatic nitrile with hydrogen at a temperature of from 150° to 250° C. and a hydrogen pressure of 1 to 50 atm (gauge pressure) in the presence of a catalyst for hydrogenation, while removing produced ammonia, wherein the catalyst contains (a) copper and (b) at least one metal selected from the group consisting of manganese, iron, cobalt, nickel and zinc in a metal weight ratio (a/b) of from 99/1 to 10/90.

The second object of the present invention is to provide a process for preparing an aliphatic secondary amine comprising reacting a $C_8$–$C_{24}$ aliphatic nitrile with hydrogen at a temperature of from 150° to 250° C. and a hydrogen pressure of 1 to 50 atm (gauge pressure) in the presence of a catalyst for hydrogenation, while removing produced ammonia, wherein the catalyst contains (a) copper and (e) the VIII group metal in a metal weight ratio (a/e) of from 1/0.0001 to 1/0.1.

The third object of the present invention is to provide a process for preparing an aliphatic primary amine comprising reacting a $C_8$–$C_{24}$ aliphatic nitrile with hydrogen at a temperature of from 150° to 250° C. and a hydrogen pressure of 1 to 50 atm (gauge pressure) in the presence of a catalyst for hydrogenation and either alkali metal hydroxide or ammonia, wherein the catalyst contains (a) copper and (e) the VIII group platinum metal and/or (f) the 4th period transition metal except for copper in a metal weight ratio (a/e) of from 1/0.0001 to 1/0.1 and (a/f) of from 99/1 to 10/90.

DETAILED DESCRIPTION OF THE INVENTION

The catalyst for hydrogenation as per the first object of the present invention comprises (a) copper and (b) at least one metal selected from the group consisting of manganese, iron, cobalt, nickel and zinc. The metal weight ratio of a/b is within the range of from 99/1 to 10/90, preferably from 99/1 to 50/50. If the metal weight ratio is outside the above range, it may hydrogenate the olefinic group in the molecule, and production efficiency becomes poor. The catalyst may contain (c) an alkali metal or an alkali earth metal in a metal weight ratio (a/c) of from 1/1 to 1/0.01, preferably from 1/0.5 to 1/0.01. Typical examples of the alkali metals are lithium, sodium, potassium, rubidium and cesium. Typical examples of the alkali earth metals are magnesium, calcium, strontium and barium. If the amount of the component (c) is more than 1/1 in a metal weight ratio based on the amount of (a), catalyst activity becomes poor. The catalyst may further contain (d) at least one metal selected from the group consisting of aluminum, molybdenum and tungsten. The metal weight ratio of a/d is preferably within the range of from 1/1 to 1/0.01. If the amount of the component d exceeds 1/1, catalyst activity is poor.

The catalyst for hydrogenation as per the second object of the present invention comprises (a) copper and (e) the VIII group metal. Typical examples of the VIII group metals are platinum, ruthenium and palladium. The metal weight ratio of a/e is preferably within the range of 1/0.0001 to 1/0.1. If the metal weight ratio is outside the above range, it may hydrogenate the olefinic groups in the molecule, thus hydrogenation selectivity being poor. The catalyst may contain (f) the 4th period transission metal except copper in a metal weight ratio (a/f) of from 99/1 to 10/90, preferably from 99/1 to 50/50. The 4th period transition metal except copper enhances the hydrogenation selectivity. Typical examples of the 4th period transition metals except copper are chromium, manganese, iron, cobalt, nickel and zinc. The catalyst may further contain (c) an alkali metal or an alkali earth metal or (e) at least one metal selected from the group consisting of aluminum, molybdenum and tungsten in the same metal weight ratio as that of the catalyst of the first object. These metals increase the catalyst activity.

The catalyst for hydrogenation of the third object of the present invention comprises (a) copper and (e) the VIII group platinum metal and/or (f) the 4th period transition metal except copper in a metal weight ratio (a/e) of from 1/0.0001 to 1/0.1 and (a/f) of from 99/1 to 10/90. The components (e) and (f) are the same as described in the above first and second object. If the amounts of the components (e) and (f) are outside the above range, both the selectivity and activity of the catalyst are poor. The catalyst may contain (c) an alkali metal or an alkali earth metal or (e) at least one metal selected from the group consisting of aluminum, molybdenum and tungsten in the same metal weight ratio as that of the catalyst of the first object. These metals increase catalyst activity.

The metal mentioned above may be contained in the catalyst of the present invention in any form, such as metal itself, metal oxide, metal hydroxide, metal salt and metal ion. In other words, the metals contained in the catalyst of the present invention are required to be in contact with the aliphatic nitrile in the reaction system irrespective of the metal form.

The catalyst of the present invention can be used in any form, such as metal itself, metal-containing material (such as, metal oxide, metal hydroxide, metal salt and metal ion) which may be carried on a carrier. The metal contained in the catalyst may be a complex stabilized by the chelation of an aliphatic carboxylic acid or a suitable ligand. The catalyst can be a combination of the above mentioned forms. Preferred is use of the metal carried on a suitable carrier, because of the stability of the catalyst metal and the durability to a catalyst poison. Such carriers are alumina, silica, silica-alumina, diatmaceous earth, active carbon, zeolite and the like. The metal may be preferably present in the carrier in an amount of from 5 to 70% by weight. A method for carrying the catalyst metal on the carrier is known in the art, for example an impregnating method wherein a carrier is poured in a solution containing a suitable metal salt for impregnating; a method wherein an alkali solution containing ammonia, sodium hydroxide, sodium carbonate and the like is added to a solution containing a carrier and a catalyst metal salt to precipitate the metal salt on the carrier; a method wherein an alkali solution and a metal salt solution are simultaneously added to a carrier slurry to precipitate the metal salt on the carrier; or an ion-exchange method wherein a catalyst metal is ion-exchanged with sodium or potassium in zeolite.

The reaction of the present invention can be carried out by contacting the catalyst for hydrogenation with the aliphatic nitrile. The contact can be accomplished in an art-known method. For example, since many aliphatic nitriles are liquid in ambient temperature, the above catalyst may be simply mixed with the aliphatic nitrile. After finishing the reaction, the catalyst can be separated from the reaction product.

The aliphatic nitrile employed in the present invention is a saturated or unsaturated aliphatic nitrile having 8 to 24 carbon atoms, such as capronitrile, lauronitrile, coconut oil fatty acid nitrile, beef fatty acid nitrile, stearonitrile, oleonitrile, linolonitrile, linoleonitrile, eruconitrile, behenonitrile or a mixture thereof. A nitrile having a branch chain which is prepared from a synthetic fatty acid having a branch chain can also be used.

The reaction can be carried out by charging the aliphatic nitrile and the catalyst for hydrogenation in a reaction vessel having a hydrogen introducing tube, a tube for sampling and a produced ammonia drain tube. The amount of the catalyst is not limited, but is preferred generally to be from 1 to 5% by weight based on the amount of the nitrile. The reaction vessel is filled with nitrogen and then substituted for hydrogen. The hydrogen pressure is controlled within 1 to 50 atm (gauge pressure), preferably 5 to 30 atm during the reaction. The reaction vessel is then heated to a reaction temperature of from 150° to 250° C., preferably from 180° to 230° C. Ammonia produced during the reaction is continuously or intermittently drained off from the reaction vessel. After the completion of the reaction, the reaction product is distilled or filtered to separate from the catalyst.

For the third object, the hydrogenation is carried out in the presence of the catalyst of the present invention and either an alkali metal hydroxide (e.g. sodium hydroxide, potassium hydroxide etc.) or ammonia. The amount of the alkali metal hydroxide is from 0.05 to 1.0% by weight based on the aliphatic nitrile. Amounts less than 0.05% by weight do not provide hydrogenation selectivity desired. Amounts more than 1.0% by weight lower catalyst activity.

According to the present invention, a long chain unsaturated aliphatic amine can be selectively prepared employing a specific catalyst in a very small amount from the corresponding unsaturated aliphatic nitrile in a short period of time. The catalyst employed in the present invention can be kept at high catalyst activity after several (ten) times of use.

EXAMPLES

The present invention is illustrated by the following examples which, however, are not construed as limiting the invention to their details.

EXAMPLE 1 AND COMPARATIVE EXAMPLE 1

A one liter flask was charged with 500 g of ion-exchanged water, 20 g of synthetic zeolite (MS-5A available from Toso Company), 30 g of copper nitrate and 10 g of zinc nitrate, and heated to 90° C. with stirring. At that temperature, 167 g of a 10% sodium carbonate aqueous solution was added dropwise and then aged for one hour. The precipitate was filtered and rinsed with water. It was then dried at 100° C. for 10 hours and baked at 700° C. for 2 hours to form a copper-zinc catalyst carried on synthetic zeolite.

Next, eruconitrile (90% purity) was hydrogenated using the obtained catalyst as follow. For comparison, the same reaction was conducted using the copper-chromium catalyst which is proposed in UK Patent 773,432.

A one liter reaction vessel having a hydrogen inlet, a sampling tube and an outlet for produced ammonia was charged with 400 g of eruconitrile and 4 g of the catalyst mentioned above and filled with nitrogen. Hydrogen was then introduced and pressured to 20 atm. The reaction vessel was heated to 180° C., keeping the hydrogen pressure at 20 atm, and the reaction was started. Ammonia produced during the reaction was intermittently drained from the reaction vessel. After the completion of the reaction, the reaction product was filtered to separate from the catalyst. The reaction product was analyzed and the results are shown in Table 1.

TABLE 1

| | Catalyst component | Reaction time (hour) | Reaction product component (wt %) | | | Olefinic bond retention %* |
| --- | --- | --- | --- | --- | --- | --- |
| | | | Unreacted eruconitrile | Secondary amine | Other component | |
| Example 1 | Copper-zinc | 12 | 1 | 90 | 9 | 98 |
| Comparative Example 1 | Copper-chromium | 12 | 23 | 65 | 12 | 90 |

*A percentage of an iodine number of the secondary amine divided by a theoretical iodine number of the secondary amine.

TABLE 2

| | Catalyst component | Reaction time (hour) | Reaction product component (wt %) | | | Olefinic bond retention % |
| --- | --- | --- | --- | --- | --- | --- |
| | | | Unreacted eruconitrile | Secondary amine | Other component | |
| Example 2 | Copper-cobalt | 20 | 1 | 88 | 11 | 95 |
| Comparative Example 2 | Copper-chromium | 20 | 32 | 58 | 10 | 91 |

It appears that the catalyst of Example 1 has higher activity and can more selectively produce a long chain unsaturated aliphatic secondary amine without hydrogenating the olefinic bond in a molecule, in comparison with Comparative Example 1.

EXAMPLE 2 AND COMPARATIVE EXAMPLE 2

A copper-cobalt catalyst was prepared as generally described in Example 1, with the exception that cobalt nitrate was employed instead of zinc nitrate. The catalyst has a copper/cobalt ratio of 5/1 and a metal support ratio of 20% (wherein metal support ratio means the metal content (wt %) based on the catalyst.).

Next, oleonitrile (96% purity) was hydrogenated using the obtained catalyst as described in Example 1, with the exception that amounts and reaction conditions are as follows. For comparison, the same reaction was conducted using the copper-chromium catalyst which is proposed in UK Patent 773,432. The results are shown in Table 2.

| Oleonitrile | 400 g |
| --- | --- |
| Copper-cobalt catalyst (Ex. 2) | 8 g |
| Copper-chromium catalyst (Comparative Ex. 2) | 8 g |
| Reaction temperature | 200° C. |
| Hydrogen pressure | 5 atm (gauge pressure) |

It appears that the catalyst of Example 2 has higher activity and can more selectively produce a long chain unsaturated aliphatic secondary amine without hydrogenating the unsaturated double bond in a molecule, in comparison with Comparative Example 2.

EXAMPLE 3 AND COMPARATIVE EXAMPLE 3

A copper-nickel-potassium catalyst was prepared as generally described in Example 1, with the exception that nickel nitrate and potassium nitrate were employed instead of zinc nitrate. The catalyst has a copper/nickel/potassium ratio of 7/1/1 and a metal support ratio of 30%.

Next, linolonitrile (90% purity) was hydrogenated using the obtained catalyst as described in Example 1, with the exception that amounts and reaction conditions are as follows. For comparison, the same reaction was conducted using the copper-chromium catalyst which is proposed in UK Patent 773,432. The results are shown in Table 3.

| Linolonitrile | 400 g |
| --- | --- |
| Copper-nickel-potassium (Ex. 3) | 12 g |
| Copper-chromium catalyst (Comparative Example 3) | 12 g |
| Reaction temperature | 210° C. |
| Hydrogen pressure | 25 atm (gauge pressure) |

It appears that the catalyst of Example 3 has higher activity and can more selectively produce a long chain unsaturated aliphatic secondary amine without hydrogenating the unsaturated double bond in a molecule, in comparison with Comparative Example 3.

EXAMPLE 4 AND COMPARATIVE EXAMPLE 4

A copper-iron-barium catalyst was prepared as generally described in Example 1, with the exception that iron nitrate and barium nitrate were employed instead of zinc nitrate. The catalyst has a copper/iron/barium ratio of 8/1/0.5 and a metal support ratio of 20%.

Next, linolenonitrile (90% purity) was hydrogenated using the obtained catalyst as described in Example 1, with the exception that amounts and reaction conditions are as follows. For comparison, the same reaction was conducted using the copper-chromium catalyst which is proposed in UK Patent 773,432. The results are shown in Table 4.

| Linolenonitrile | 400 g |
| --- | --- |
| Copper-iron-barium (Ex. 4) | 12 g |
| Copper-chromium catalyst (Comparative Example 4) | 12 g |
| Reaction temperature | 210° C. |
| Hydrogen pressure | 35 atm (gauge pressure) |

It appears that the catalyst of Example 4 has higher activity and can more selectively produce a long chain unsaturated aliphatic secondary amine without hydrogenating the unsaturated double bond in a molecule, in comparison with Comparative Example 4.

TABLE 3

| | Catalyst component | Reaction time (hour) | Reaction product component (wt %) | | | Olefinic bond retention % |
|---|---|---|---|---|---|---|
| | | | Unreacted eruconitrile | Secondary amine | Other component | |
| Example 3 | Copper-nickel-potassium | 5 | 0 | 92 | 8 | 92 |
| Comparative Example 3 | Copper-chromium | 5 | 15 | 73 | 12 | 88 |

TABLE 4

| | Catalyst component | Reaction time (hour) | Reaction product component (wt %) | | | Olefinic bond retention % |
|---|---|---|---|---|---|---|
| | | | Unreacted eruconitrile | Secondary amine | Other component | |
| Example 4 | Copper-iron-barium | 3 | 0 | 90 | 10 | 93 |
| Comparative Example 4 | Copper-chromium | 3 | 8 | 79 | 13 | 85 |

EXAMPLES 5 AND 6

A copper-manganese-aluminum catalyst was prepared as generally described in Example 1, with the exception that manganese nitrate and aluminum nitrate were employed instead of zinc nitrate. The catalyst has a copper/manganese/aluminum ratio of 8/1/0.5, a metal support ratio of 20%.

Next, caprylonitrile (98% purity) and branched nitrile (a branched nitrile having 18 carbon atoms derived from branched fatty acid available from Emery Company as Emasol 871) were hydrogenated using the catalyst obtained in Example 1, with the exception that amounts and reaction conditions are as follows. The results are shown in Table 5.

| | |
|---|---|
| Caprylonitrile (Ex. 5) | 400 g |
| or | |
| Branched nitrile (Ex. 6) | 400 g |
| Copper-manganese-aluminum | 12 g |
| Reaction temperature | 210° C. |
| Hydrogen pressure | 25 atm (gauge pressure) |

It appears that the catalyst of Examples 5 and 6 has higher activity and can more selectively produce a long chain unsaturated aliphatic secondary amine without hydrogenating the unsaturated olefinic bond in a molecule.

EXAMPLE 7

This example shows the durability of activity and selectivity of the catalyst obtained in Example 1 after repetitive cycles (5 times) of catalyst use and its successive recovery.

Oleonitrile (90% purity) was hydrogenated five times, with the exception that amounts and reaction conditions are as follows. The results are shown in Table 6.

| | |
|---|---|
| Catalyst/oleonitrile (wt %) | 2/100 |
| Reaction temperature | 210° C. |
| Hydrogen pressure | 5 atm (gauge pressure) |

It appears that the catalyst has a good activity and can selectively produce a long chain unsaturated aliphatic secondary amine without hydrogenating the olefinic bond in a molecule, even after repeatedly using (five times).

TABLE 5

| | Reactant nitrile | Reaction time (hour) | Reaction product component (wt %) | | |
|---|---|---|---|---|---|
| | | | Unreacted nitrile | Secondary amine | Other component |
| Example 5 | Caprylonitrile | 7 | 1 | 94 | 5 |
| Example 6 | Branched nitrile | 10 | 0 | 93 | 7 |

TABLE 6

| | Catalyst component | Reaction time (hour) | Reaction product component (wt %) | | | Olefinic bond retention % |
|---|---|---|---|---|---|---|
| | | | Unreacted oleonitrile | Secondary amine | Other component | |
| Example 7 | Copper-zinc | 20 | 2 | 91 | 7 | 97 |

EXAMPLES 8 AND 9 AND COMPARATIVE EXAMPLE 5

A copper-ruthenium catalyst was prepared as generally described in Example 1, with the exception that 30 mg of ruthenium chloride was employed instead of zinc nitrate. The catalyst has a copper/ruthenium ratio of 30/0.04 and a metal support ratio of 28%.

A copper-rhodium catalyst was prepared as generally described in Example 1, with exception that rhodium chloride was employed instead of zinc nitrate. The catalyst has a copper/rhodium ratio of 31/0.04 and a metal support ratio of 28%.

Next, eruconitrile (90% purity) was hydrogenated using the obtained catalysts as described in Example 1, with the exception that amounts and reaction conditions are as follows. For comparison, the same reaction was conducted using the copper-chromium catalyst which is proposed in UK Patent 773,432. The results are shown in Table 7.

| | |
|---|---|
| Eruconitrile | 400 g |
| Copper-ruthenium (Ex. 8) or | 4 g |
| Copper-rhodium (Ex. 9) | 4 g |
| Copper-chromium catalyst (Comparative Example 5) | 4 g |
| Reaction temperature | 180° C. |
| Hydrogen pressure | 20 atm (gauge pressure) |

It appears that the catalysts of Examples 8 and 9 have higher activity and can more selectively produce a long chain unsaturated aliphatic secondary amine without hydrogenating the unsaturated double bond in a molecule, in comparison with Comparative Example 5.

TABLE 7

| | | Reaction | Reaction product component (wt %) | | | |
|---|---|---|---|---|---|---|
| | Catalyst component | time (hour) | Unreacted eruconitrile | Secondary amine | Other component | Olefinic bond retention % |
| Example 8 | Copper-ruthenium | 9 | 0 | 90 | 10 | 90 |
| Example 9 | Copper-rhodium | 9 | 0 | 89 | 11 | 89 |
| Comparative Example 5 | Copper-chromium | 12 | 23 | 65 | 12 | 90 |

EXAMPLES 10 AND 15 AND COMPARATIVE EXAMPLE 6

The copper-The 4 period transition metal (chromium, manganese, iron, cobalt, nickel or zinc)-rhodium catalysts of the present invention were prepared as generally described in Example 1. The metal components, metal weight ratio and metal support ratio of the catalyst are shown in Table 8.

TABLE 8

| Example No. | Catalyst | Metal weigh ratio | Metal support ratio (%) |
|---|---|---|---|
| 10 | Cu—Cr—Rh | Cu/Cr/Rh = 2/1/0.01 | 20 |
| 11 | Cu—Mn—Rh | Cu/Mn/Rh = 4/1/0.03 | 20 |
| 12 | Cu—Fe—Rh | Cu/Fe/Rh = 7/1/0.03 | 20 |
| 13 | Cu—Co—Rh | Cu/Co/Rh = 7/1/0.03 | 20 |
| 14 | Cu—Ni—Rh | Cu/Ni/Rh = 8/1/0.01 | 20 |

TABLE 8-continued

| Example No. | Catalyst | Metal weigh ratio | Metal support ratio (%) |
|---|---|---|---|
| 15 | Cu—Zn—Rh | Cu/Zn/Rh = 4/1/0.05 | 20 |

Next, oleonitrile (96% purity) was hydrogenated as generally described in Example 1, using the obtained catalysts, with the exception that amounts and reaction conditions are as follows. For comparison, a similar reaction was conducted using the copper-chromium catalyst which is proposed in UK Patent 773,432. The results are shown in Table 9.

| | |
|---|---|
| Oleonitrile | 400 g |
| The catalysts (Examples 10 to 15) | 8 g |
| Copper-chromium catalyst (Comparative Example 6) | 8 g |
| Reaction temperature | 200° C. |
| Hydrogen pressure | 20 atm (gauge pressure) |

TABLE 9

| | Reaction time (hour) | Reaction product component (wt %) | | | Olefinic bond retention % |
|---|---|---|---|---|---|
| | | Unreacted eruconitrile | Secondary amine | Other component | |
| Example 10 | 7 | 1 | 94 | 5 | 92 |
| Example 11 | 7 | 1 | 92 | 7 | 91 |
| Example 12 | 7 | 0 | 95 | 5 | 92 |
| Example 13 | 6 | 1 | 93 | 6 | 95 |
| Example 14 | 6 | 0 | 95 | 5 | 90 |
| Example 15 | 7 | 0 | 96 | 4 | 93 |
| Comparative Example 6 | 10 | 3 | 85 | 12 | 90 |

It appears that the catalysts of Examples 10 to 15 have higher activity and can more selectively produce a long chain unsaturated aliphatic secondary amine without hydrogenating the unsaturated double bond in a molecule, in comparison with Comparative Example 6.

EXAMPLES 16 AND 19 AND COMPARATIVE EXAMPLE 7

The copper-cobalt-platinum-the alkali metal or alkali earth metal catalysts of the present invention were prepared as generally described in Example 1. The metal components, metal weight ratio and metal support ratio of the catalyst are shown in Table 10.

TABLE 10

| Example No. | Catalyst | Metal weight ratio | Metal support ratio (%) |
|---|---|---|---|
| 16 | Cu—Co—Pt—K | Cu/Co/Pt/K = 7/1/0.01/0.5 | 30 |
| 17 | Cu—Co—Pt—Cs | Cu/Co/Pt/Cs = 7/1/0.01/0.8 | 30 |
| 18 | Cu—Co—Pt—Ca | Cu/Co/Pt/Ca = 8/1/0.02/0.5 | 30 |
| 19 | Cu—Co—Pt—Ba | Cu/Co/Pt/Ba = | 30 |

TABLE 10-continued

| Example No. | Catalyst | Metal weigh ratio | Metal support ratio (%) |
|---|---|---|---|
| | Ba | 8/1/0.02/0.5 | |

Next, linolonitrile (90% purity) was hydrogenated as generally described in Example 1, using the obtained catalysts, with the exception that amounts and reaction conditions are as follows. For comparison, the same reaction was conducted using the copper-chromium catalyst which is proposed in UK Patent 773,432. The results are shown in Table 11.

| | |
|---|---|
| Linolonitrile | 400 g |
| The catalysts (Examples 16 to 19) | 12 g |
| Copper-chromium catalyst (Comparative Example 7) | 12 g |
| Reaction temperature | 210° C. |
| Hydrogen pressure | 10 atm (gauge pressure) |

TABLE 11

| | Reaction time (hour) | Reaction product component (wt %) | | | Olefinic bond retention % |
|---|---|---|---|---|---|
| | | Unreacted eruconitrile | Secondary amine | Other component | |
| Example 16 | 9 | 0 | 98 | 2 | 93 |
| Example 17 | 9 | 1 | 96 | 3 | 92 |
| Example 18 | 9 | 1 | 97 | 2 | 91 |
| Example 19 | 9 | 0 | 96 | 4 | 94 |
| Comparative Example 7 | 9 | 8 | 84 | 8 | 90 |

It appears that the catalysts of Examples 16 to 19 have higher activity and can more selectively produce a long chain unsaturated aliphatic secondary amine without hydrogenating the unsaturated double bond in a molecule, in comparison with Comparative Example 7.

EXAMPLES 20 AND 21

A copper-zinc-palladium-aluminum catalyst was prepared as generally described in Example 1. The catalyst has a Cu/Zn/Pd/Al ratio of 8/2/0.2/0.5 and a metal support ratio of 50%.

Next, caprylonitrile (98% purity) and branched nitrile (a branched nitrile having 18 carbon atoms derived from branched fatty acid available from Emery Company as Emasol 871) were hydrogenated using the obtained catalyst as described in Example 1, with the exception that amounts and reaction conditions are as follows. The results are shown in Table 12.

| | |
|---|---|
| Caprylonitrile (Ex. 20) or | 400 g |
| Branched nitrile (Ex. 21) | 400 g |
| The catalyst | 12 g |
| Reaction temperature | 210° C. |
| Hydrogen pressure | 20 atm (gauge pressure) |

It appears that the catalysts of Examples 20 and 21 have higher activity and can more selectively produce a long chain unsaturated aliphatic secondary amine without hydrogenating the unsaturated double bond in a molecule.

EXAMPLE 22

This example shows the durability of catalyst and selectivity of hydrogenation of the catalyst obtained in the following manner after 5 times (cycles) i.e. repetitions of catalyst use and its successive recovery.

A copper-zinc-ruthenium catalyst was prepared as generally described in Example 3 with the exception that Zn nitrate and ruthenium chloride were employed. The catalyst has a copper/zinc/ruthenium ratio of 8/2/0.02 and a metal support ratio of 20%.

Oleonitrile (90% purity) was hydrogenated five times, with the exception that amounts and reaction conditions are as follows. The results are shown in Table 13.

| | |
|---|---|
| Catalyst/oleonitrile (wt %) | 2/100 |
| Reaction temperature | 200° C. |
| Hydrogen pressure | 20 atm (gauge pressure) |

It appears that the catalyst has good activity and can selectively produce a long chain unsaturated aliphatic secondary amine without hydrogenating the unsaturated double bond in a molecule, even after repeatedly using the catalyst (five times).

TABLE 12

| | Reactant nitrile | Reaction time (hour) | Reaction product component (wt %) | | |
|---|---|---|---|---|---|
| | | | Unreacted nitrile | Secondary amine | Other component |
| Example 20 | Caprylo-nitrile | 5 | 0 | 94 | 6 |
| Example 21 | Branched nitrile | 7 | 0 | 92 | 8 |

TABLE 13

| | Catalyst component | Reaction time (hour) | Reaction product component (wt %) | | | Olefinic bond retention % |
|---|---|---|---|---|---|---|
| | | | Unreacted oleonitrile | Secondary amine | Other component | |
| Example 22 | Cu—Zn—Ru | 6 | 0 | 95 | 5 | 95 |

PRODUCTION EXAMPLE 1

A one liter flask was charged with 50 g of ion-exchanged water, 20 g of synthetic zeolite (MS-5A), 50 g of copper nitrate, 10 g of zinc nitrate and 50 mg of ruthenium chloride, and heated to 90° C. with stirring. At that temperature, 255 g of a 10% sodium carbonate aqueous solution was added dropwise and then aged one hour. The precipitate was filtered and rinsed with water. It was then dried at 100° C. for 10 hours and baked at 500° C. for 2 hours to form a copper-zinc-ruthenium catalyst carried on synthetic zeolite.

PRODUCTION EXAMPLES 2 TO 5

Copper-rhodium-The 4 period metal (manganese, iron, cobalt or nickel)-lithium catalysts were prepared as generally described in Production Example 1. All catalysts had a metal weight ratio (Cu/Rh/The 4 period metal/Li) of 8/0.5/1/0.5.

PRODUCTION EXAMPLE 6

A copper-zinc catalyst was prepared as generally described in Production Example 1, with the exception that rhodium chloride was not employed. The catalyst had a metal weight ratio (Cu/Zn) of 9/1.

EXAMPLES 23 TO 28

A one liter reaction vessel having a hydrogen inlet, a sampling tube and an outlet for produced ammonia was charged with 300 g of oleonitrile or stearonitrile, sodium hydroxide (0.2% by weight) and the catalyst mentioned above and filled with nitrogen. Hydrogen was then introduced and pressurized to a pressure as shown in Table 14. The reaction vessel was heated to a temperature as shown in Table 14, keeping the hydrogen pressure, and the reaction was started. After the completion of the reaction, the reaction product was filtered to separate from the catalyst. The reaction product was analyzed and the results are shown in Table 14.

COMPARATIVE EXAMPLES 8 AND 9

Same experiments were conducted as generally described in Examples 23 to 28, with the conditions as shown in Table 14. The analysis and double bond retention are shown in Table 14.

It appears that the catalysts of Examples 23 to 28 have higher activity and can more selectively produce a long chain unsaturated aliphatic secondary amine without hydrogenating the unsaturated double bond in a molecule, than those of with Comparative Examples 8 and 9.

What is claimed is:

1. A process for preparing an unsaturated aliphatic secondary amine comprising reacting a $C_8$-$C_{24}$ unsaturated aliphatic nitrile with hydrogen at a temperature of 150° to 250° C. and a hydrogen pressure of 1 to 50 atm (gauge pressure) in the presence of a catalyst for hydrogenation, while removing produced ammonia, wherein the catalyst contains (a) copper, (b) at least one metal selected from the group consisting of nickel, zinc and cobalt and (e) a Group VIII metal selected from the group consisting of platinum, palladium, rhodium, and ruthenium in a metal weight ratio (a/b) of from 99 to 10/90 and (a/e) of from 1/0.0001 to 1/0.1.

2. The process according to claim 1 wherein said catalyst further contains (c) an alkali or alkaline earth metal in a metal weight ratio (a/c) of from 1/1 to 1/0.01.

3. The process according to claim 1 wherein said catalyst further contains (d) at least one metal selected from the group consisting of aluminum, molybdenum and tungsten in a metal weight ratio (a/d) of from 1/1 to 1/0.01.

4. A process for preparing an unsaturated aliphatic primary amine comprising reacting an unsaturated $C_8$-$C_{24}$ aliphatic nitrile with hydrogen at a temperature of 150° to 250° C. and a hydrogen pressure of 1 to 50 atm (gauge pressure) in the presence of a catalyst for hydrogenation, while removing produced ammonia, wherein the catalyst contains (a) copper, (b) at least one metal selected from the group consisting of nickel, zinc and cobalt and (e) a Group VIII metal selected from the group consisting of platinum, palladium, rhodium, and ruthenium in a metal weight ratio (a/b) of from 99 to 10/90 and (a/e) of from 1/0.0001 to 1/0.1.

5. The process according to claim 4 wherein said catalyst further contains (c) an alkali or alkaline earth metal in a metal weight ratio (a/c) of from 1/1 to 1/0.01.

6. The process according to claim 4 wherein said catalyst further contains (d) at least one metal selected from the group consisting of aluminum, molybdenum and tungsten in a metal weight ratio (a/d) of from 1/1 to 1/0.01.

TABLE 14

|  |  | Example No. |  |  |  |  |  | Comparative Example No. |  |
|---|---|---|---|---|---|---|---|---|---|
|  |  | 23 | 24 | 25 | 26 | 27 | 28 | 8 | 9 |
| Catalyst |  | Production Example No. |  |  |  |  |  | Raney-Ni | Raney-Ni |
|  |  | 1 | 2 | 3 | 4 | 5 | 6 |  |  |
| Nitrile |  | Oleo-nitrile | Stearo-nitrile | Stearo-nitrile | Stearo-nitrile | Stearo-nitrile | Oleo-nitrile | Oleo-nitrile | Oleo-nitrile |
| Percentage of the catalyst (wt %) |  | 1 | 2 | 2 | 2 | 2 | 2 | 1 | 1 |
| Hydrogen pressure (gauge press.) |  | 20 | 10 | 10 | 10 | 10 | 20 | 20 | 20 |
| Reaction temperature (°C.) |  | 210 | 210 | 210 | 210 | 210 | 210 | 210 | 130 |
| Reaction time (h) |  | 6 | 7 | 7 | 7 | 6 | 8 | 2 | 4 |
| Reaction product component (wt %) | Unreacted Oleonitrile | 0 | 2 | 1 | 0 | 0 | 0 | 0 | 0 |
|  | Primary amine | 96 | 94 | 92 | 95 | 94 | 94 | 92 | 93 |
|  | Other component | 4 | 4 | 7 | 5 | 6 | 6 | 8 | 7 |
| Olefinic bond retention (%) |  | 98 |  |  |  |  | 92 | 0 | 80 |

UNITED STATES PATENT AND TRADEMARK OFFICE
CERTIFICATE OF CORRECTION

PATENT NO. : 5,097,073

DATED : March 17, 1992

INVENTOR(S) : Hiroshi ABE et al.

It is certified that error appears in the above-identified patent and that said Letters Patent is hereby corrected as shown below:

On the title page, item (54) in the title:

Amend "PRODUCTION OF ALIPHATIC PRIMARY OF SECONDARY AMINE"

to
--PRODUCTION OF ALIPHATIC PRIMARY OR SECONDARY AMINE--

Signed and Sealed this

Seventeenth Day of August, 1993

Attest:

BRUCE LEHMAN

Attesting Officer  Commissioner of Patents and Trademarks